United States Patent
Raksi

(10) Patent No.: US 7,330,275 B2
(45) Date of Patent: Feb. 12, 2008

(54) METHOD AND SYSTEM FOR DETERMINING THE POSITION AND ALIGNMENT OF A SURFACE OF AN OBJECT IN RELATION TO A LASER BEAM

(75) Inventor: Ferenc Raksi, Irvine, CA (US)

(73) Assignee: Intralase Corp., Santa Ana, CA (US)

( * ) Notice: Subject to any disclaimer, the term of this patent is extended or adjusted under 35 U.S.C. 154(b) by 0 days.

(21) Appl. No.: 11/271,089

(22) Filed: Nov. 12, 2005

(65) Prior Publication Data
US 2006/0114469 A1    Jun. 1, 2006

Related U.S. Application Data

(63) Continuation of application No. 10/269,340, filed on Oct. 11, 2002, now Pat. No. 6,992,765.

(51) Int. Cl.
*G01B 11/02* (2006.01)
(52) U.S. Cl. .................................. 356/508; 356/510
(58) Field of Classification Search ................ 356/496, 356/508, 510
See application file for complete search history.

(56) References Cited

U.S. PATENT DOCUMENTS

| | | | |
|---|---|---|---|
| 4,794,585 A | 12/1988 | Lee | |
| 5,338,924 A | 8/1994 | Barrett et al. | |
| 5,446,538 A | 8/1995 | Noll | |
| 5,457,533 A | 10/1995 | Wilcken | |
| 5,532,815 A | 7/1996 | Kipman et al. | |
| 5,541,731 A * | 7/1996 | Freedenberg et al. | 356/496 |
| 5,673,281 A | 9/1997 | Byer | |
| 5,739,906 A * | 4/1998 | Evans et al. | 356/503 |
| 6,303,903 B1 | 10/2001 | Liu | |
| 6,355,908 B1 | 3/2002 | Tatah et al. | |
| 6,373,571 B1 | 4/2002 | Juhasz et al. | |
| 6,545,761 B1 * | 4/2003 | Aziz et al. | 356/497 |
| 6,594,006 B1 | 7/2003 | Muehlhoff et al. | |
| 2002/0103481 A1 | 8/2002 | Webb et al. | |
| 2004/0102765 A1 | 5/2004 | Koenig | |

FOREIGN PATENT DOCUMENTS

| | | |
|---|---|---|
| EP | 1 034 755 A | 9/2000 |
| EP | 1 078 710 A2 | 2/2001 |

OTHER PUBLICATIONS

M.H. Niemz, et al.; *Intrastromal ablations for refractive corneal surgery using picosecond infrared laser pulses*; Lasers and Light in Ophthalmology vol. 5 No. 3, pp. 149-155; 1993.

* cited by examiner

*Primary Examiner*—Tarifur Chowdhury
*Assistant Examiner*—Marissa J Detschel
(74) *Attorney, Agent, or Firm*—Townsend & Townsend & Crew LLP; Mark D. Barrish

(57) ABSTRACT

The present invention generally relates to a method and system for determining the position and alignment of a plane in relation to an intersecting axis and using that known position and alignment to allow for corrections to be made when using the plane as a reference plane. More particularly, the invention relates to a method and system for determining the angle of tilt of a planar surface in relation to a laser beam, and using the determined angle of tilt to calculate a correction factor to be applied to the laser beam. Briefly stated, the method and system ultimately calculates a correction factor, z-offset, that is applied when using the laser beam in a procedure.

7 Claims, 4 Drawing Sheets

METHOD AND SYSTEM FOR DETERMINING THE POSITION AND ALIGNMENT OF A SURFACE OF AN OBJECT IN RELATION TO A LASER BEAM

PRIORITY

Priority as a continuation application is claimed to U.S. application Ser. No. 10/269,340, now U.S. Pat. No. 6,992,765, filed Oct. 11, 2002. The disclosure of the priority application is incorporated herein by reference as if set forth in full.

BACKGROUND OF THE INVENTION

1. Field of the Invention

The field of the present invention is laser focusing systems and methods.

2. Background

Various laser procedures or operations require that a laser beam be properly focused to a specific focal point. For example, in ophthalmic laser surgery wherein eye tissue is to be photodisrupted or ablated in or on the tissue that is to be affected, the correct positioning of a focusing assembly used to focus a laser beam is very critical. Such ophthalmic surgical procedures include those in cornea, sclera, iris, the crystalline lens and related structures, vitreous, and retina, and for treatment of glaucoma. Focal depth precision is also required in many non-ophthalmic laser surgical procedures, such as applications in dermatology and even "surgery" in DNA to excise portions of chromosomes. Also, non-biologic applications, such as photolithography and micromachining require focal depth precision.

With presently used laser systems, however, it is a critical concern that the object be positioned in a known relationship relative to the laser system. For example, in eye surgery, it is only when the eye can be positioned in a known relationship relative to the laser system that the laser beam can be directed to the desired area inside the eye with a high degree of accuracy. This is important because an inaccurately or improperly directed laser beam could affect an area of the eye not desired to be treated and cause permanent damage to the eye.

One way to accurately position the eye relative to a laser system for the purposes of performing laser ophthalmic procedures is to use a contact lens to stabilize the eye. To do this, however, the alignment of the contact lens (glass plate or "aplanation lens") relative to the laser system must be known. As indicated above, if the lens alignment relative to the laser beam is not known, errors in accurate positioning of the laser beam can result.

In order to ensure that the alignment of a contact lens is known relative to a laser system, it is possible to permanently mount the lens on the laser system in a fixed orientation. If the contact lens is to remain mounted on the laser system, however, sterilization of the lens after each laser ophthalmic procedure could be time consuming, difficult to accomplish and, most likely, very uneconomical. Alternatively, the contact lens could be removed from the laser system, sterilized, and replaced. Further, a disposable contact lens could be used for the laser ophthalmic procedure. For either of these last two alternatives, however, the contact lens will require realignment with the laser system after the lens is mounted on the laser system.

U.S. Pat. No. 6,373,571 (incorporated herein by reference for all purposes) issued to Juhasz et al., discloses a system and method for aligning an aplanation lens with a laser system. In particular, Juhasz discloses that in order to properly align the aplanation lens to a laser system, reference marks on the contact lens are brought into coincidence with predetermined focal points along the laser beam paths. To this end, the laser system successively directs a laser beam along at least three predetermined paths to respective predetermined focal points, and the contact lens is positioned across these predetermined paths. Along each predetermined path, the laser beam is activated to establish a series of laser marks on the contact lens. If the laser marks, predetermined focal points, and reference marks are all coincident, then the contact lens is properly aligned with the laser system. If there is any displacement between any laser mark and reference mark, however, a retainer ring holding the aplanation lens is adjusted to align all reference marks with all predetermined focal points to align the lens to the laser system.

Because of the foregoing, it is however desirable to have alternative system and methods to determine the position and alignment of a plane of an object in relation to an intersecting axis and using that known position and alignment to allow for corrections to be made when using the plane as a reference plane.

SUMMARY OF THE INVENTION

The present invention generally relates to a method and system for determining the position and alignment (including the angle and orientation of tilt) of a plane of an object in relation to an intersecting axis and using that known position and alignment to allow for corrections to be made when using the plane as a reference plane. More particularly, the invention relates to a method and system for determining the position and alignment of a planar surface of an object in relation to a laser beam, and using the determined position and alignment to calculate a correction factor to be applied to the laser beam focal point. The method and system can also be adapted for objects with curved surfaces. Briefly stated, the method and system ultimately calculates a correction factor, z-offset, that is applied when using the laser beam in a procedure, such as photodisrupting corneal tissue below an aplanation lens.

Once the position and alignment of the aplanation lens is determined, the positioning of the laser beam can be corrected to take the alignment into account when using the laser beam to photodisrupt corneal tissue. In general the method can be broken into two steps: first, determining the position and alignment of the aplanation lens relative to the laser beam; second, determining the corrected position of the laser beam z-offset for later use in a procedure.

In one aspect of the inventive system, the movement of the focal point of the laser beam is controlled by a CPU and software instructions. The software instructions may be contained on storage media such as CDs, hard drives, diskettes, or other electronic storage media devices. Additionally, the computer software (instruction sets) may be stored in ROM, RAM or other storage devices capable of storing computer instructions. A software program may be configured to capture the z-axis location of the occurrence of detected plasma sparks. In addition to the z-axis location, the position of the x-axis and y-axis location may be captured.

Various laser sources may be used with the inventive method and system, including infrared, visible, and UV lasers. Further, laser sources to be used with the inventive method and system may be continuous wave, Q-switched pulse, and mode-locked ultrashort pulse lasers. Although the foregoing is not an exhaustive list, lasers of the foregoing type may be used with the present invention. In one aspect of the invention the laser beam is formed of a continuously repeating train of short optical pulses in the range of femtoseconds or picoseconds. In one embodiment, the laser source is an infrared ultrashort pulse laser with a pulse duration of less than 10 picoseconds. While various laser sources may be utilized, in one femtosecond laser system, the laser energy per pulse to photodisrupt the object and create a plasma spark is about 1-5 μJ for a focus of 2.5 μm.

The object used with the present invention is a material capable of producing a detectable plasma spark when contacted with the focal point of a laser beam. Some materials where a plasma spark may be created include glass, silicon, or plastic (including medical grade plastic), and biologic materials. The object is either permanently or temporarily affixed to the laser system such that the object falls within the path of the laser beam. A cage, base, frame, or other holding device may be used to position the object in place. For example, an aplanation lens composed of highly purified fused silica is placed in a cone shaped frame which is connected to the laser system as described in co-pending U.S. application Ser. No. 09/772,539 (Publication No. US2002/0103481) and Ser. No. 09/896,429 (Publication No. US2002/0103482) (the disclosures of which are incorporated herein for all purposes). Another example is a microscope slide positioned in place by using pressure to hold the slide in place.

In one aspect of the invention, there is a method and system for determining the occurrence of a plasma spark about the surface of an object, or within the object. The method and system utilizes a photodetector to detect the occurrence of the plasma spark when the focal point of the laser beam contacts the surface of the object, or when the laser beam is focused within the object. The photodetector identifies when a plasma spark occurs. The photodetector may be any one of a photodiode, CCD, photomultiplier, phototransistor, or any device suited for detecting the occurrence of a plasma spark.

In one aspect of the invention, there is a method and system for determining the position and alignment of a surface of an object in relation to a laser beam. A laser system for generating a laser beam and an object having a substantially planar surface are provided. The method and system may also be adapted for objects with a curved surface. The object is positioned in the path of the laser beam. The object may be permanently or temporarily affixed to the laser system. The focal point of the laser beam is repeatedly moved along a predetermined pattern in a plane perpendicular to a z-axis of the laser beam. Plasma sparks are detected when the laser beam focal point contacts the object. The position and alignment of the surface of the object in relation to the laser beam is determined.

In one aspect of the invention, moving the focal point of the laser beam includes starting at a starting point on a z-axis plane such that the focus of the laser beam is not in contact with the object; repeatedly moving the focal point of the laser beam along a predetermined pattern in at least one plane perpendicular to the z-axis; and after an occurrence of the completion of movement of the laser beam along the predetermined pattern, repositioning the focal point of the laser beam on the z-axis a set distance Δz from the previous z-axis location. The predetermined pattern is preferably circular in shape. In one embodiment, the focal point of the laser beam may be positioned below the object and the laser beam moved up towards the object. Or in another embodiment, the focal point of the laser beam may be focused somewhere between the laser source and the object, and the laser beam moved towards (or downward) to the object.

In another aspect of the invention, detection of plasma sparks includes identifying a first plasma spark when the laser beam comes into contact with the object; recording a first z-axis location of the first plasma spark; identifying the completion of the predetermined pattern by identifying a second plasma spark along the complete predetermined pattern; and recording a second z-axis location of the second plasma spark.

Further to detecting the plasma sparks, the position and alignment of the object in relation to the z-axis using the first z-axis location and the second z-axis location is calculated. In one embodiment, calculation of the tilt angle (alignment) of a surface of an object is performed by utilizing the formula $\theta = \tan^{-1}(\Delta z/D)$, where $\Delta z$ is the difference between the first z-axis location and the second z-axis location, and D is the diameter of the predetermined pattern.

In one embodiment of the invention, plasma sparks are visually detected by the operator. The occurrence of a first plasma spark and the occurrence of a second plasma spark at the completion of a predetermined pattern are detected. An input device such as a foot switch interconnected with the laser system is manually operated. When the operator of the laser system visually identifies the first occurrence of a plasma spark, then the input device is triggered to signal to the computer to record the first z-axis position. The laser focal point continues through the object in iterative predetermined patterns. When the operator of the laser system visually identifies the completion of the predetermined pattern, then the operator actuates the input device, which in turn triggers the computer to record the second z-axis position.

In another embodiment of the invention, the detection of the plasma spark includes providing a photodetector for detecting plasma sparks, and identifying the occurrence of the plasma spark with the photodetector. The photodetector may be any one of a photodiode, CCD, photomultiplier, phototransistor, or any device suited for detecting the occurrence of a plasma spark.

In one embodiment of the invention, the detection of the plasma spark includes providing a video camera for taking images of the object and capturing a series of images of the object. The position and alignment of the surface can be determined by subtracting the pixels of a previous image from the pixels of a current image and subsequently adding all the resulting pixels that exceed a certain threshold to become a final number for that image which correlates with the plasma intensity for that image. The final number for each calculation may be plotted on a graph to establish a plasma intensity curve.

The step of determining the alignment of the aplanation lens relative to the laser beam can be broken into several substeps, as follows. First, if the z-axis is defined as the path of the laser beam, the focal point of the laser is directed on the z-axis below the aplanation lens, at a point $z_0$. The focal point of the laser beam is then moved along a closed pattern, for example, a circle with a fixed diameter less than the diameter of the aplanation lens, in a plane perpendicular to the z-axis. After the focal point has completed the closed pattern, the focal point is adjusted at a set distance (also referred to as a separation layer), $z_x$, above to $z_1$, and the moving step is repeated. These last two steps, adjusting the focal point up the z-axis to $Z_2$ and moving the focal point in the closed pattern, are repeated i times until the focal point of the laser is adjusted up the z-axis to $z_i$ and the focal point makes contact with the aplanation lens, causing a plasma spark. When this occurs, the position of the focal point, $z_i$ is recorded. The focal point is then adjusted $z_x$ above the previous starting point and the focal point is moved along the closed pattern in a plane perpendicular to the z-axis until the laser makes contact with the aplanation lens along the entire closed pattern, causing a plasma spark along the entire closed pattern. When this occurs, the position of the focal point, $z_j$, is again recorded. A $\Delta z$ can be determined, by calculating the distance between $z_0$ and $z_j$. Using the diameter of the closed pattern and the total distance along the z-axis the focal point traveled, trigonometry can be used to determine the angle, $\theta$, of the aplanation lens relative to the z-axis.

In one aspect of the invention, a method and system for determining the alignment of a surface of an object in relation to a laser beam is disclosed. An object having a substantially planar surface is provided. A laser system for generating a laser beam is utilized to create at least three plasma sparks at the surface of the object. The laser system has a CPU with software configured to carry out the process and computations. The plasma sparks may be detected in any manner, including those described previously, such as manually/visually, a photodetector, or the video image analysis. By detecting three points about the planar surface of the object, it is possible to identify a plane in relation to a z-axis of the laser beam and the plane's tilt relative to the laser beam z-axis. Additionally, the curvature of a surface may be detected if the surface is not planar. In this case, multiple points would be identified with plasma sparks and their x-,y-,z-coordinates recorded. The curvature of the surface may then be computed.

In one aspect of the invention, a method and system for determining a focal point of a laser beam upon an object having a substantially planar surface is disclosed. The novel system and method utilizes an interferometer to determine a fringe pattern of a reflection of a laser beam from the object. In this particular system and method, an object having a substantially planar surface is provided. A laser system for generating a laser beam is provided. The laser system has a central processing unit configured for instructing movement of the laser beam. The interferometer is interconnected with the laser system. The laser beam is focused at or near the substantially planar surface. The laser beam is reflected back from the planar surface. A fringe pattern is detected. Based on the analysis of the fringe pattern, the laser beam is determined to be in or out of focus. A software program for execution on the central processing unit may be configured for focusing the laser beam at or near the substantially planar surface of the object, detecting a fringe pattern of the laser beam, and determining whether the laser beam is in focus based on the fringe pattern. If the fringe pattern lines are substantially parallel to one another, then the laser beam is focused on the planar surface.

In yet another aspect of the invention, another method and system for determining a focal point of a laser beam upon an object having a substantially planar surface is disclosed. The laser system computer monitors the dependence of the signal on depth. Change in the signal indicates the interface between the lower surfaces of the aplanation glass and the cornea. A laser system for generating a laser beam has a central processing unit configured for instructing movement of the laser beam. A photomultiplier with a band pass filter for detecting a nonlinear frequency signal generated by the laser beam is interconnected with the laser system. A software program for execution on the central processing unit is configured for monitoring a nonlinear frequency signal generated by the laser beam, and determining whether the laser beam is in focus. The nonlinear frequency signal may be any one of second harmonic generation, third harmonic generation, stimulated Raman, or white light generation and others.

In yet another aspect of the invention, a method and system for determining the distance between two objects is disclosed. A laser system for generating a laser beam having a central processing unit configured for instructing movement of the laser beam is utilized to create and detect a first plasma spark at the surface of a first object, and to create and detect a second plasma spark at the surface of a second object. A software program is configured for identifying a first point at the outer surface of a first object by detecting the occurrence of a first plasma spark; identifying a second point at the outer surface of the second object by detecting the occurrence of a second plasma spark; and determining the distance between the first point and the second point. The software program records the x-,y, z-axis location of the first and second points, and then calculates the distance between the points. The detection of the plasma spark may be done by any device capable of detecting a plasma spark. In one embodiment, the plasma spark is detected by a photodetector. Some examples of a photodetector includeany one of a photodiode, CCD, photomultiplier, phototransistor, or any device suited for detecting the occurrence of a plasma spark.

BRIEF DESCRIPTION OF THE DRAWINGS

For a more complete understanding of the present invention, reference is now made to the following descriptions taken in conjunction with the accompanying drawings, in which.

DETAILED DESCRIPTION OF THE INVENTION

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

Figure 1:
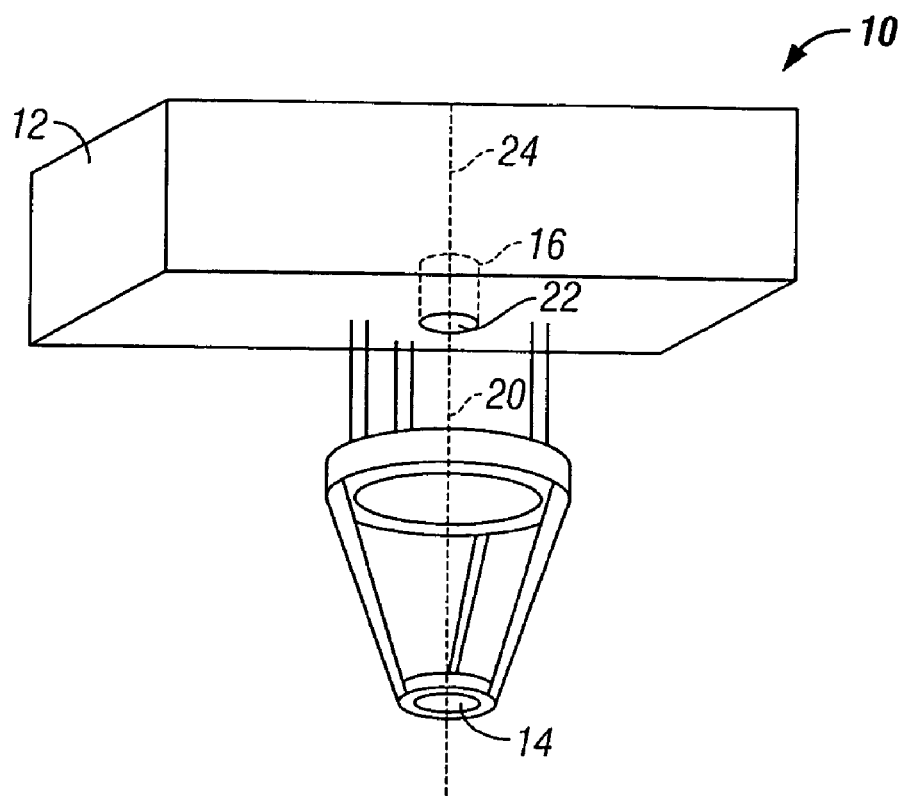
FIG. 1 is a perspective view of the system used to determine position and alignment of the aplanation lens relative to the laser system illustrating an embodiment of the present invention.

Referring now to FIG. 1, a schematic view of one embodiment of an aplanation lens position and alignment system according to the present invention is depicted. The major components of the system 10 are a laser system 12 and an aplanation lens 14. To accomplish laser ophthalmic surgery, the laser system 12 includes a laser source 16 which is mounted on the system housing (not shown). This laser source 16 generates a laser beam 20 from an origination point 22, as shown in FIG. 1. In one embodiment of the invention, the laser beam 20 has a pulse duration less than three hundred picoseconds (<300 ps) and a wavelength of between approximately 400-3000 nm. Preferably, the laser operates at 1053 nm, with a pulse duration of approximately 600-800 femtoseconds, and a repetition rate of 10 kHz. FIG. 1 shows that the laser beam 20 is used to define a z-axis 24 that is parallel to the path of the laser beam. As discussed herein, the inventive system and method are shown through the use of an aplanation lens. However, the position and alignment of other objects may be determined. Thus, the inventive system and method should be construed to cover any other object for which one wants to determine its position and alignment in relation to a laser beam.

Determination of Object Alignment

Figure 2:
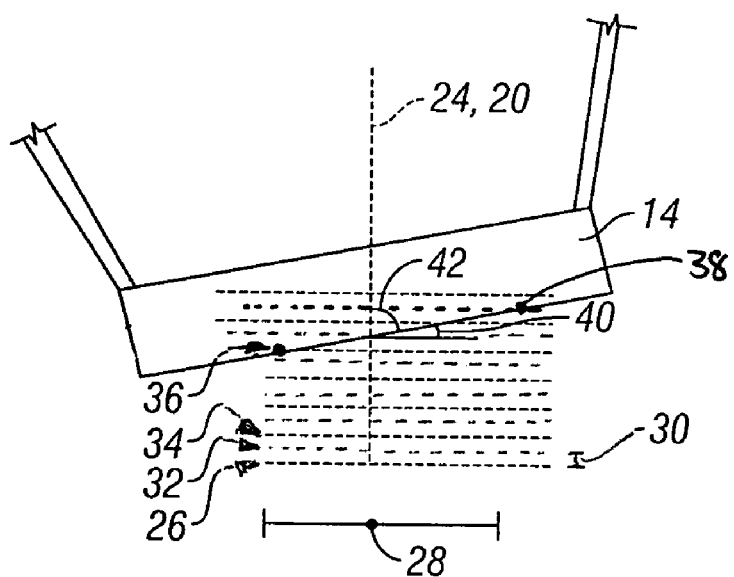
FIG. 2 is a schematic view of the aplanation lens and the laser beam.

Referring to FIG. 2, a schematic view of a laser beam 20 and tilted aplanation lens 14 is shown. To determine the position and alignment of the aplanation lens 14 in relation to the z-axis 24 of the laser beam, the focal point of the laser beam is first directed to a point on the z-axis 24 that is below the aplanation lens 14. This first point is referred to as $z_0$ 26. The focal point of the laser beam is then moved along a closed pattern. The closed pattern is a shape where the laser beam focal point will travel. As the laser beam focal point travels along the closed pattern, the laser beam is fired. A spot distance of the laser beam may be set by the laser system such that the laser beam is fired on the closed pattern for a particular distance. For example, in one embodiment, the spot distance may be set to 1 µm-30 µm. For a particular object and laser source being utilized, the spot distance may be different than the aforementioned example.

In a preferred embodiment, the closed pattern is a circular shape having a diameter ("D") 28. The closed pattern is made in a plane perpendicular to the z-axis 24. For an ophthalmic procedure using the aplanation lens, the closed pattern should have a diameter sufficiently wide, such that after the position of the aplanation lens and alignment determination is completed, a cornea then pressed against the aplanation lens does not contact an area of the closed pattern. In certain tests using an aplanation lens, a 7-9.5 mm diameter was utilized for the closed pattern and was found sufficiently wide. Other diameters of course may be utilized depending on the type of procedure and the particular object for which alignment is being determined.

After the first closed pattern is completed, the focal point of the laser beam is then adjusted up the z-axis 24 a set distance $z_x$ 30 to another starting point $z_1$ 32 where $z_1 = z_0 + z_x$. The value for the $z_x$ distance between each successive closed pattern is also referred as a separation layer distance. For each pass of the closed pattern, the laser beam focal point will move a distance along the z-axis based on the separation layer setting.

The focal point of the laser beam is then again moved along a similar closed pattern in a plane perpendicular to the z-axis 24 and then adjusted up the z-axis to $z_2$ 34 where $Z_2 = z_1 + z_x$. The steps of moving the focal point along the closed pattern and adjusting the starting point of the focal point of the laser beam up the z-axis 24 are repeated n times, until the focal point of the laser along the closed pattern makes contact with the aplanation lens 14, causing a first plasma spark, at $z_n$ 36, which may be detected. The particular manner in which the plasma sparks are detected is described below.

A CPU utilizing software preferably instructs the movement of the focal point of the laser beam. While moving the laser beam, the software may record the coordinates of the focal point. For example, as the closed pattern is followed, the specific x-, y- and z-coordinates of the laser beam focal point will be known. This is true because it is the software instructing the movement of the focal point through the closed pattern at particular coordinates. Thus, the laser system software may be configured or programmed to record the x, y, and/or z-coordinates based on certain defined events.

The particular $z_n$ when the first plasma spark occurs is recorded. The steps of moving the focal point along the closed pattern and adjusting the starting point of the focal point of the laser beam up the z-axis 24 are repeated m times, until the focal point of the laser contacts the aplanation lens 14 along the entire closed pattern, causing a plasma spark along the entire closed pattern, at $z_j$ 38, where j=m+n, which is detected. The point $z_j$ is recorded. The particular manner in which detection of the completion of the closed pattern occurs is later described below.

Figure 3:
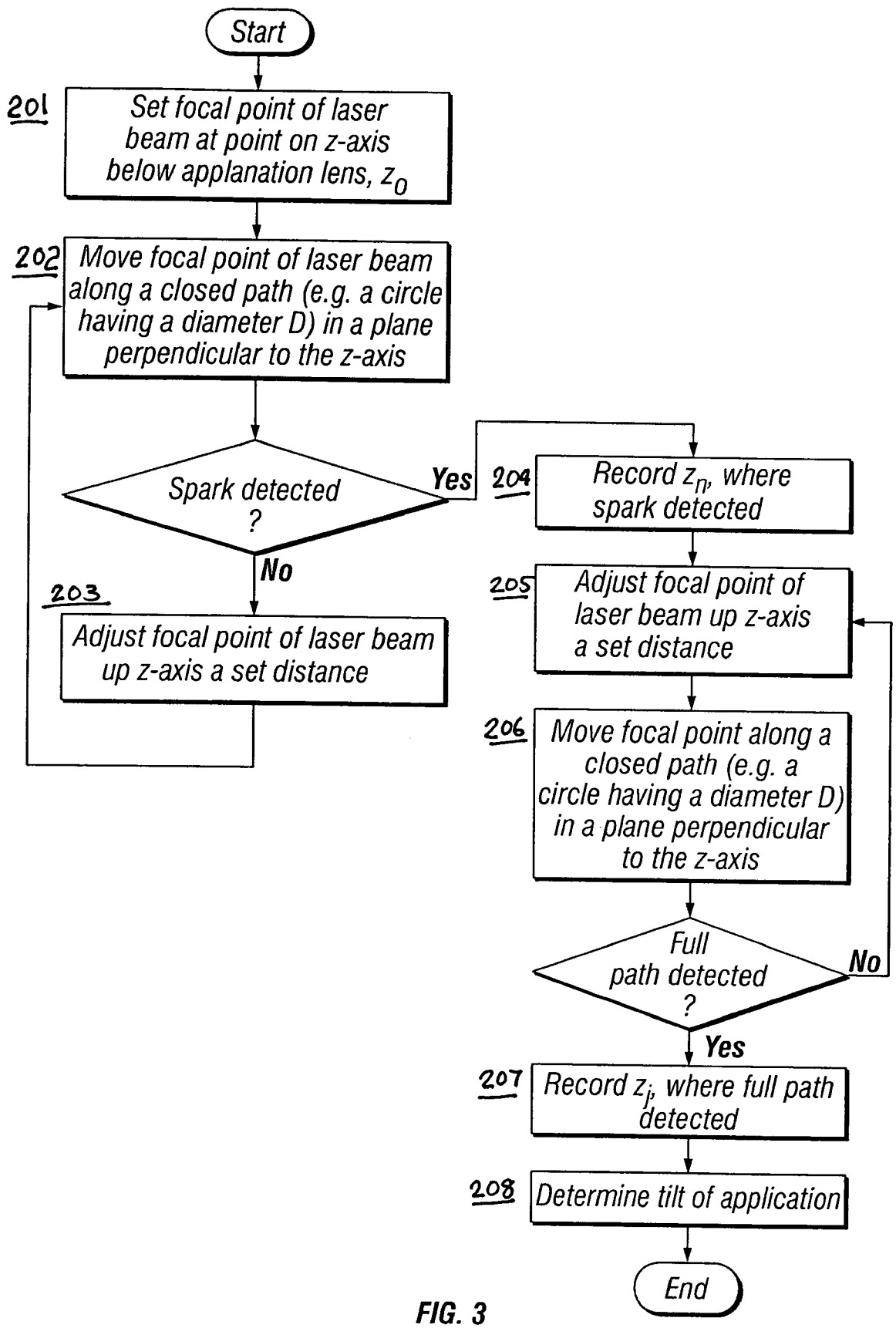
FIG. 3 is a flowchart illustrating a method for determining the position, alignment, and orientation of the aplanation lens relative to the focal plane of the laser beam.

For a better understanding of the inventive method, FIG. 3 sets out in flowchart form certain steps of the present invention. In step 201, the focal point of the laser beam is set at a point on the z-axis below the aplanation lens, $z_0$. Next in step 202, the focal point of the laser beam is moved along a pattern, preferably in the shape of a circle having a diameter D, in a plane perpendicular to the z-axis. During the movement of the laser beam along the pattern, a check is made for the occurrence of a plasma spark. If a plasma spark is detected, then in Step 204, the $z_n$ location is recorded. Likewise, the $x_n$ and $y_n$ coordinates may also be recorded. If no spark is detected, when the pattern is complete, then in Step 203 the focal point of the laser beam is moved up the z-axis a determined distance, $z_x$. Step 202 is repeated until a plasma spark is detected.

In Step 205, the focal point of the laser beam is moved up the z-axis a determined distance, $z_x$. Then in Step 206, the focal point of the laser beam is moved along a predetermined pattern, preferably in the shape of a circle having a diameter D, in a plane perpendicular to the z-axis. During the movement of the laser beam along the pattern, a check is made for the occurrence of a completion of a plasma spark for the circumference of the circle. If a completion of the entire circle is detected, then in Step 207, the $z_j$ location is record. Also, the location of the $x_n$ and $y_n$ coordinates may also be recorded. If the completion of the plasma spark for the circumference of the circle is not completed, then Step 205 repeats. Lastly, in Step 208, the tilt of the aplanation lens can be determined.

Visual Detection of Plasma Spark

The plasma spark may be visually detected by the operator. For example, a foot switch operated by the user of the laser system may identify when the plasma spark occurs. The movement of the focal point along the closed pattern is performed as discussed above. When the user first detects the plasma spark, a foot switch may be activated. The activation of the switch signals the computer to record the z-axis coordinate of the first plasma spark. When the user detects completion of the closed pattern by watching a complete plasma spark along the closed pattern, the user activates the foot switch again. Thus, the second z-axis coordinate is obtained. With both coordinates the tilt of the lens may then be determined.

Electronic Detection of Plasma Spark

In another embodiment, a photodetector connected with the laser system may be utilized to detect the occurrence of plasma sparks. The photodetector can be any device capable of determining such an event. For example, a photodetector may include a photodiode, CCD, photomultiplier, phototransistor, or any device suited for detecting the occurrence of a plasma spark.

The photodetector can be utilized to determine a first occurrence of the plasma spark and the completion of the closed pattern, thereby giving first and second z-axis coordinates which then may be used to calculate the tilt of the aplanation lens.

In one embodiment, a photodetector is connected with the laser system. The photodetector is placed in a position on, adjacent to, or near the laser system where the photodetector can detect the plasma spark. The photodetector generates a voltage or signal when the laser beam creates a plasma spark in the aplanation lens. When the photodetector first detects a plasma spark, then the laser system software records the first z-axis coordinate.

For the second z-axis position at the completion of the plasma spark along all of the closed pattern, the identification of the completion may be determined in different ways. One way to determine the completion of the closed pattern is to evaluate the voltage or signal from the photodetector and compare it with a known time for completion of the closed pattern. The laser system software may be configured to calculate the duration of time necessary to complete a given closed pattern. At the completion of the closed pattern, the voltage or signal of the photodetector can be evaluated. If the voltage or signal of the photodetector indicates that a plasma spark is occurring at the end of the closed pattern, then we know that a plasma spark has occurred at the end of the closed pattern. With this known completion point, then the second z-axis position can be determined.

Information about the orientation of tilt can be obtained by determining the x-y coordinate where the most intense plasma spark is detected within the object. The strongest signals from the plasma spark correspond to the deepest position within the object.

Video Image Detection of Plasma Spark

In an alternative embodiment, a video camera is utilized to capture images of the aplanation lens as plasma sparks are being generated. By comparing sequences of captured images, it is then possible to use the image information to determine the tilt of the aplanation lens. In one embodiment, an NTSC camera with a rate of 30 frames per second was utilized. However, other video cameras with different frame rates may be utilized.

In general, video images are searched for plasma spark as the laser beam focal point is scanned upwards toward the bottom surface of the aplanation lens. Similar to the visual/manual and photodetector methods described above, the laser beam focal point is set at a beginning point such that the focal point of the laser beam does not create a plasma spark. The laser beam focal point is then moved through successive closed patterns whilst first and second z-axis coordinates are determined.

In one embodiment, 8-bit grey scale images are captured and evaluated. A grey scale image has pixels with a grey scale value between 0 (black) and 255 (white). The grey scale values ranging between 0-255 indicates the brightness for a particular pixel. For example, if an area of certain pixels of an image had a value of zero or near zero, this would indicate that portion of the image was dark. If an area of certain pixels had a value of 255 or near 255, this would indicate that portion of the image was very light. Thus the higher the number for the pixels of a certain area of an image, the brighter (or whiter) that area would be. Based on this pixel valuation model, the occurrence of a plasma spark can be detected. When a plasma spark occurs and an image is taken, more higher-ranging pixels would exist than would exist if the plasma spark was not occurring. This is because the plasma spark creates a very bright light that would be noted in the image.

Figure 4:
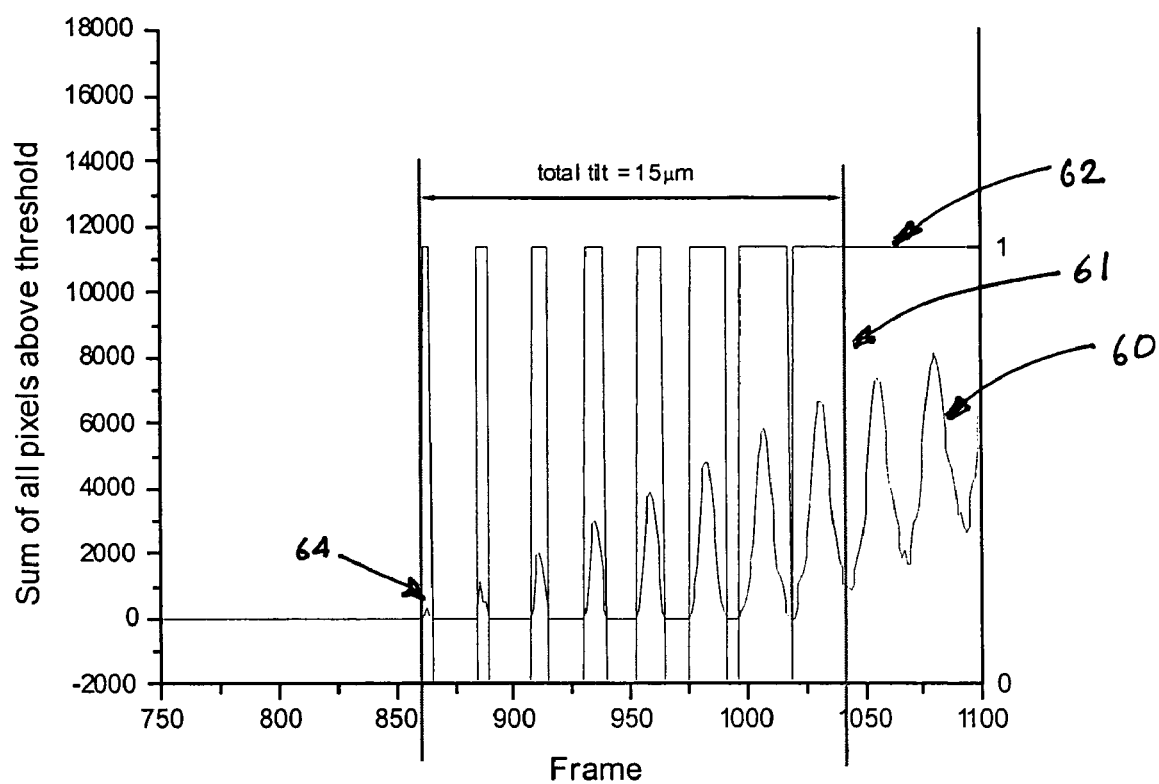
FIG. 4 is a graph illustrating a video image analysis for determining the position, alignment, and orientation of an aplanation lens relative to laser beam.

Referring now to FIG. 4, a graph is shown illustrating an aplanation lens tilt determination utilizing the iterative image comparison method. The frequency of image frames to be captured is set at a periodic time interval. The x-axis on the graph represents the frame number of a captured video image. In the illustrated example, a focal point of the laser beam was set in a circular pattern with a diameter of 7.8 mm. The spot distance of the laser was set at 3 µm. An energy level of 3 µJ energy for the laser source was utilized. The y-axis on the graph represents the Total Compared Image Value, for those pixels above a certain threshold number. In the experiment, the threshold number was set at a value of 20.

The plasma spark line 60 shows the processing of several frames of images before, during and after the occurrence of plasma sparks. The video image process begins with the capture of a first video image. After a preset time interval, the next image is captured. The first video image and the second video image are then compared to one another.

Each pixel value (0-255) from the first image is added together to obtain a first image value. Also, each pixel value (0-255) from the second image is added together to obtain a second image value. If a threshold value is set, then only those pixel values having a value higher than the threshold value would be added together. Utilizing a threshold value reduces the light noise dramatically and allows the process to run at full room light and high illumination of the aplanation lens.

The first image value is subtracted from the second image value giving a Total Compared Image Value. The Total Compared Image Value, which is stored in memory of the CPU, may be plotted on a graph. Although not shown on the graph, for a Total Compared Image Value, the laser system software would also know or have stored the x-,y-, and z-coordinates for the particular image frame. Thus, for a particular Total Compared Image Value, the x-, y-, and z-coordinates may be associated with the particular Total Compared Image Value.

As illustrated in FIG. 4, prior to about frame 860, no plasma spark has occurred. On the y-axis, the plasma spark line is shown as a linear line having a Total Compared Image Value of zero. During the process the ambient light is preferably maintained at a consistent level. As shown in FIG. 4, literally no noise signal exists before the plasma starts, even at full room light. As the plasma spark starts, from about frame 860, the increasing mountains of signals occur as is shown on plasma spark line 60.

The spacing between each side of a mountain on the plasma spark line 60 represents the completion of one full circle. The first mountain 64 indicates the first occurrence of a plasma spark. The exact x-y coordinates at any mountain top gives the tilt axis. The first time the mountain does not go down to 0 (or some low threshold), the plasma circle is completed (second or final contact).

To more easily detect the first and the second contact, the plasma spark line 60 is further processed in the following way. A binary signal (or plasma spark state) may be created with the following process. The binary signal or plasma spark state is set to one 1 if the Total Compared Image Value is over a certain value. If for a particular image frame, the Total Compared Image Value is greater than the set value (in the example it was set to 1), then for that frame the plasma spark state would be set to 1 or True. If the Total Compared Image Value is below the set value, then the plasma spark state would be set to 0 or False. In this manner, as shown on the graphed plasma spark state line 62, the state of the plasma spark for a particular image frame and time would be known.

The distance between two consecutive mountain peaks is equivalent to the layer separation parameter defined by the laser software. This is usually in the order of 2-10 micrometers but may vary according to the desired accuracy. For each mountain peak, the closed pattern makes one revolution and for each revolution, the focus position moves upward in the z-direction in the amount of the layer separation. The amount of peaks contained between the first plasma spark 64 and the full closure of the pattern 61 determines the following $\Delta z = |z_{(1st\ plasma)} - z_{(Full\ closure)}|$. The determination of the tilt axis is dependent on the position of the x-y coordinate at the time the mountain peak is present. An axis line can be drawn 180° from the x-y position of the mountain peak, relative to the center of the circular pattern. The determination of tilt is as follows $\theta = \tan^{-1}(\Delta z/D)$ where $\Delta z$ is the difference of z position between the first plasma spark 64 and the full closure of the pattern 61 as detected by the CCD camera and D is the diameter of the circular pattern.

Calculation of Tilt of the Lens and Z-Coordinate Offset

The alignment of the aplanation lens 14 in relation to the z-axis 24 is then calculated by using the following equation: $\theta = \tan^{-1}(\Delta z/D)$; where $\theta$ 40 is the angle between the aplanation lens 14 and a plane perpendicular to the z-axis 24, and wherein $\Delta z$ is the difference between the first z-axis location and the second z-axis location, and D is the diameter of the predetermined pattern. The angle $\phi 42$ between the z-axis 24 and the aplanation lens 14 is $90-\theta$.

Although the methods above discuss obtaining a second z-axis location by electronic or manual means, the second z-axis may be calculated. After the first z-axis location is found, then the second z-axis is calculated. The second z-axis location would be the point on a circular predetermined pattern opposite the first z-axis location. This holds true since, by using a circular predetermined pattern, the first z-axis location is the lowest point of the tilt (if scanning the laser from the below the aplanation lens upwards) and the highest point would always be the point on the predetermined pattern opposite the first z-axis location. Thus, the first z-axis location may be determined (along with the x-,y-coordinates) and then using the known diameter of the circular pattern, the second z-axis location may be determined.

Utilizing the circular predetermined pattern, by finding the first and second z-axis location, the plane of the contact surface of the aplanation lens can be determined along with the orientation of the plane about the z-axis.

Determining the tilt of the aplanation lens 14 in relation to the laser beam is very useful. In the field of ophthalmic surgery, a more precise photodisruption of tissue of the eye can be achieved. For example, it is important in ophthalmic laser surgery procedures that photodisruption be very precise. Whilst utilizing an aplanation lens, a patient's cornea is pressed against the lens, thereby flattening the cornea against the glass surface of the lens. With a perfectly calibrated laser system, using a perfectly formed aplanation lens, the contact surface (the contact plane) of the aplanation lens would be perpendicular to the laser beam. This would allow the focusing of the laser beam at a z-coordinate in the cornea in one x-y location to be the same z-coordinate if the laser focus was moved to another x-y location. But if the aplanation lens were tilted, this would cause the focus of the laser at one x-y location in the tissue of eye to actually be different than another x-y location in the tissue of the eye. But if the tilt of the aplanation lens were known, then the z-coordinate (or focal depth) for a particular x-y location could be offset or compensated for to take into consideration the lens tilt.

Three-Point Method to Determine Tilt of an Object

An alternative way to determine the tilt of a surface of an object in relation to a z-axis of a laser beam is to determine three points of an object. A laser beam may be focused at a z-axis point such that the focal point of the laser beam does not contact the object. This may be at any x-,y-coordinate. The laser beam z-axis focal point is incrementally moved a specified distance and the laser fired. The focal point is moved again a set distance and fired. This continues until a first plasma spark is detected. The detection may be by any manner, including the method described above, manually, via photodetector, and video image comparison. The first point (its x-,y-, and z-coordinates) is recorded or saved in memory or storage by the laser system.

The laser system then directs the laser beam to a second x,y-coordinate. The focal point of the laser is then moved to a z-axis point such that the focal point of the laser beam does not contact the object. Then again, the laser beam z-axis focal point is incrementally moved a specified distance and the laser fired. This continues until a second plasma spark is detected. The second point (its x-,y-, and z-coordinates) is recorded or saved in memory or storage by the laser system.

The laser system then directs the laser beam to a third x,y-coordinate. The focal point of the laser beam is then moved to a z-axis point such that the focal point of the laser beam does not contact the object. Then again, the laser beam z-axis focal point is incrementally moved a specified distance and the laser fired. This continues until third plasma spark is detected. The third point (its x-,y-, and z-coordinates) is recorded or saved in memory or storage by the laser system.

Having now determined three surface points of a surface of the object, a plane of the surface in relation to a z-axis of the laser be would be known. Knowing the plane of the object, then subsequent procedures can use the plane as a reference plane for z-offset.

Also, the distance between two points may be calculated by detecting a first plasma spark at the surface of a first object, and detecting a second plasma spark at the surface of a second object. The detection of the first and second plasma spark may be detected by the methods described above. The z-axis coordinate of each plasma spark is then used the determined the distance between the surface of each object where the plasma spark is detected.

Z-offset and Gain Calibration Procedure

By determining the alignment (or tilt) of a surface of an object in relation to a laser beam (or z-axis of the laser beam), a z-offset value may be utilized for subsequent laser system operations. For a particular x-,y-coordinate, the z-coordinate may be offset a particular distance to allow the focus of the laser beam to be at a plane parallel to the plane of the tilt of the object.

In one embodiment, a software program commands a displacement of a focusing assembly of a laser system by writing a voltage to a Digital/Analog card. A z-Galvo will in turn move the focusing assembly to the desired focal depth position based upon the commanded voltage by directing a current to the motor-driven focusing assembly. A linear encoder positioned within the laser system senses the linear movement of the focusing assembly. An intelligent controller interoperating with the host computer and software program utilizes a sensor to read an encoder strip attached to the focusing assembly. As the lens is moved into position, encoder feedback is provided by an intelligent controller and an actual focusing assembly position is obtained.

To measure the z-gain, a second point needs to be measured. Measurement of the z-gain may be achieved by utilizing a second object, such as glass that has a substantially planar top and bottom surface that are substantially parallel to one another.

In one experiment, a 160 μm thick microscope slide was mounted against the contact glass of the aplanation lens contact plane. The slide was made out of borosilicate glass (Corning 0211) with a refractive index of 1.521 at 1060 nm. The flatness of the slide was measured. It had parallel top and bottom planar surface within ±1 μm over the whole slide (22×22 mm). The slide is pressed against the contact glass by slightly pushing from below with a rod and a round plastic screw head on top of it. This results in an air gap below the slide at the circle diameter of the closed pattern. The circular closed patterns are now cut like in the z-offset procedure except that the starting depth is set at 200 μm. This simulates focusing the laser beam into the corneal tissue. To correct for the human cornea (n=1.377), the 160 μm thick borosilicate glass corresponds to a 146 μm thick cornea layer. This was simulated with the WinLase™ 3.0 Pro software using a Gaussian beam with an f#=1.48 focusing number of the objective lens.

With the correction in place, the software is expected to report an offset of 146 μm if the z-offset was zeroed before a procedure. If the number is off, then the z-scale factor (z-gain) is off by the following amount: New z-scale factor= (146 μm/measured offset)*old z-scale factor After correcting the z-scale factor in the laser system settings, the z-offset needs to be redone because it might not fall together with a 0-voltage on the z-scanner and therefore can be affected by a gain change.

Interferometric Laser Focus Detection

Another way to measure the position of a surface of an object relative to a laser beam is utilizing an interferometer. After measurement, the laser system may then account for variances of height dimensions of the object and set offset parameters for the focal depth. Offset parameters in software allow canceling the effect of variances of height dimensions of the aplanation lens, thereby delivering consistent surgical depths.

This method utilizes the curvature of the wave front of a laser reflected back from the glass surface of the aplanation lens. The curvature of the wave front is measured by an interferometer.

There are two ways to relate fringe curvatures to focal depth. First, by knowing the geometry of the optics and the interferometer, the fringe patterns can be exactly calculated and related to focal depths. However this method would require a precise knowledge of the beam geometry.

A second, more practical method is to calibrate the machine to measurable focal positions. This is the approach we followed with our implementation. In one implementation the machine is set to cut patterns in a glass sample at different depths while the interference patterns are simultaneously recorded. Then the cutting depths in the sample are measured with the help of a microscope and related to the curvatures of the fringes as previously recorded.

The interferometer utilizes a reference beam, which is split directly from the laser beam before entering the delivery system, and a measured beam, which passes through the delivery system. The reference beam is essentially a parallel beam. The measured beam is part of the laser beam that reflects back from the optical surface of the aplanation lens. The reflected beam retraces the optical path through the laser focusing optics and the scanner system in a backward direction.

If the reflecting surface is at the focal point, then the back-reflected beam retraces the same path all the way through the delivery system and leaves it as a parallel beam. This beam can be interfered with a reference beam. In this case, both beams are parallel and they make an interference pattern with straight fringes. On the other hand, if the aplanation lens is out of focus, then the back-reflected beam does not trace the very same path backwards, and it leaves the delivery system as a convergent or divergent beam. Convergent or divergent beams combined with parallel beams produce curved fringe patterns. The position information of the focus can be extracted from the interference pattern, essentially from the sign and magnitude of the curvature of the fringes.

In one embodiment an image processing method is followed. A raw image is first captured then filtered and enhanced by convoluting the image with a spatially periodic kernel. This process smoothes imperfections of the image which are of random nature for example due to dust particles on the optics. At the same time the spatial periodicity of the kernel enhances the contrast of the interference pattern with the right periodicity.

The next step of the image processing is edge detection by Canny Edge Detection algorithm. (Canny, A. (1986) A computational approach to edge detection. IEEE Trans. PAMI, 8:769-698.)

The edge fragments are then analyzed. Fragments shorter than a given length are discarded. The longer fragments are fitted with a polynomial curve. The second order coefficient of the polynomial gives the curvatures of the individual fringes. Finally curvatures from individual fringes are averaged.

In one embodiment, the interference pattern is captured by a video camera and frame capture software described above. The pattern may be analyzed by computer software. The curvature of the fringe pattern is extracted and the focal position calculated. To determine the focal position, when the fringe pattern has parallel beams, then the laser beam is focused. One way to determine how much the laser beam is out of focus, is the mass calibrate various curvatures of the fringe pattern and measure the focal distance. For example, a micrometer may be used to determine the various focal distance for a particular fringe curvature. For a particular fringe curvature, a focal depth value may be stored in a table. Then for subsequent uses of the laser system, a particular fringe pattern curvature, may be determined and then looked up in the table to determine the focal position. Alternatively, for the curvature behavior could be evaluated to determine an algorithm, such that for a particular fringe curve a focal position could be derived.

Figure 5A:
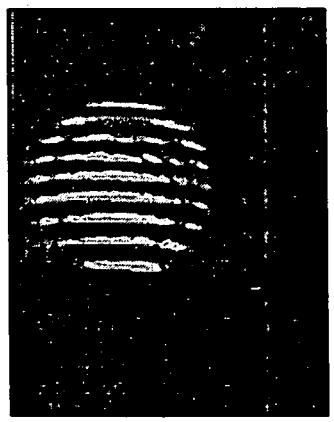
FIG. 5A-5C are drawings illustrating detected pattern fringes while using an interferometer for focusing a laser beam.
Figure 5B:
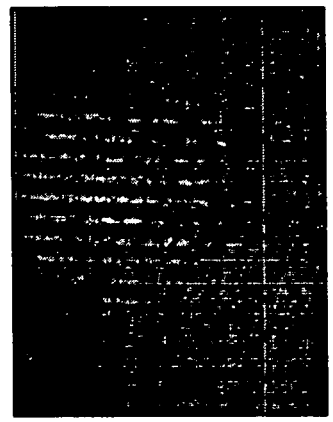
Figure 5C:
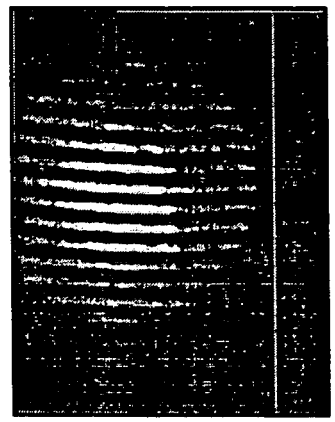

Various experiments were performed to determine the fringe patterns and the relation to the focus of the laser beam. In one experiment, the measured interference fringe pattern curved downwards. This is shown in FIG. 5A. The focus of the laser beam was found to be 20 μm above the contact plane of the aplanation lens. In another experiment, the measured interference fringe pattern formed straight lines. This is shown in FIG. 5B. The focus of the laser beam was found to be on the glass surface of the aplanation lens. In a third experiment, the measured fringe pattern curved upwards. This is shown in FIG. 5C. The focus of the laser beam was found to be 10 μm below the contact plane of the aplanation lens.

Measuring one point at the optical center of the field of view of the aplanation lens provides a z-offset number. This method may be used to measure three point measurements of the contact plane of the aplanation lens to determine the tilt of the focal plane.

This interferometric method not only has the advantage of determining the focal point of a plane of an aplanation lens, but also may be used to detect laser beam distortions. Some of these distortions may be i) inherent to the design of the laser system optics, such as spherical and chromatic aberrations, ii) coming from the laser, such as spatial chirp, iii) distortions from component level aberrations, such as out of spec mirror flatness, or iv) distortions due to system misalignment.

If the measured focal position of the laser is outside of a pre-determined acceptable range, the laser system software may be configured to instruct the servo system to modify offset values for the z-axis focal position and then bring the laser system into an acceptable range. Also, the software parameters for a surgical pattern may be configured to accommodate hardware offset and tilt of the laser focal plane relative to a surgical plane.

Nonlinear Frequency Conversion

Another method to determine the depth of focus of a laser beam is utilizing a photo multiplier with band pass filter to monitor the nonlinear frequency signal generated by laser beam. The laser system computer monitors the dependence of the signal on depth of focal point. Change in the signal indicates the interface between the lower surfaces of the aplanation glass and the cornea. Nonlinear frequency conversion method is noninvasive. The depth calibration can be performed while the aplanation lens is docked on a patient's eye thus reducing the error introduced by mechanical backlashes.

This method is based on usage of different nonlinear effects in glass and the cornea to generate light at frequencies other than the frequency of the laser beam. The effects can include, but not be limited to, second harmonic generation, third harmonic generation, stimulated Raman, white light generation and others. At laser beam intensities close to photodisruption threshold, conversion efficiencies of mentioned nonlinear processes are high enough to generate a detectable signal. These signals have quadratic or higher order dependence on input intensity and will be confined in space to the beam waist and will therefore increase the accuracy of interface detection.

A photo multiplier with a band pass filter is attached to the laser system. The computer of the laser system monitors the dependence of the signal on focal point depth. A change in the signal indicates the interface between the lower surface of the aplanation lens and cornea. Accuracy of better than 5 microns may be achieved.

Figure 6:
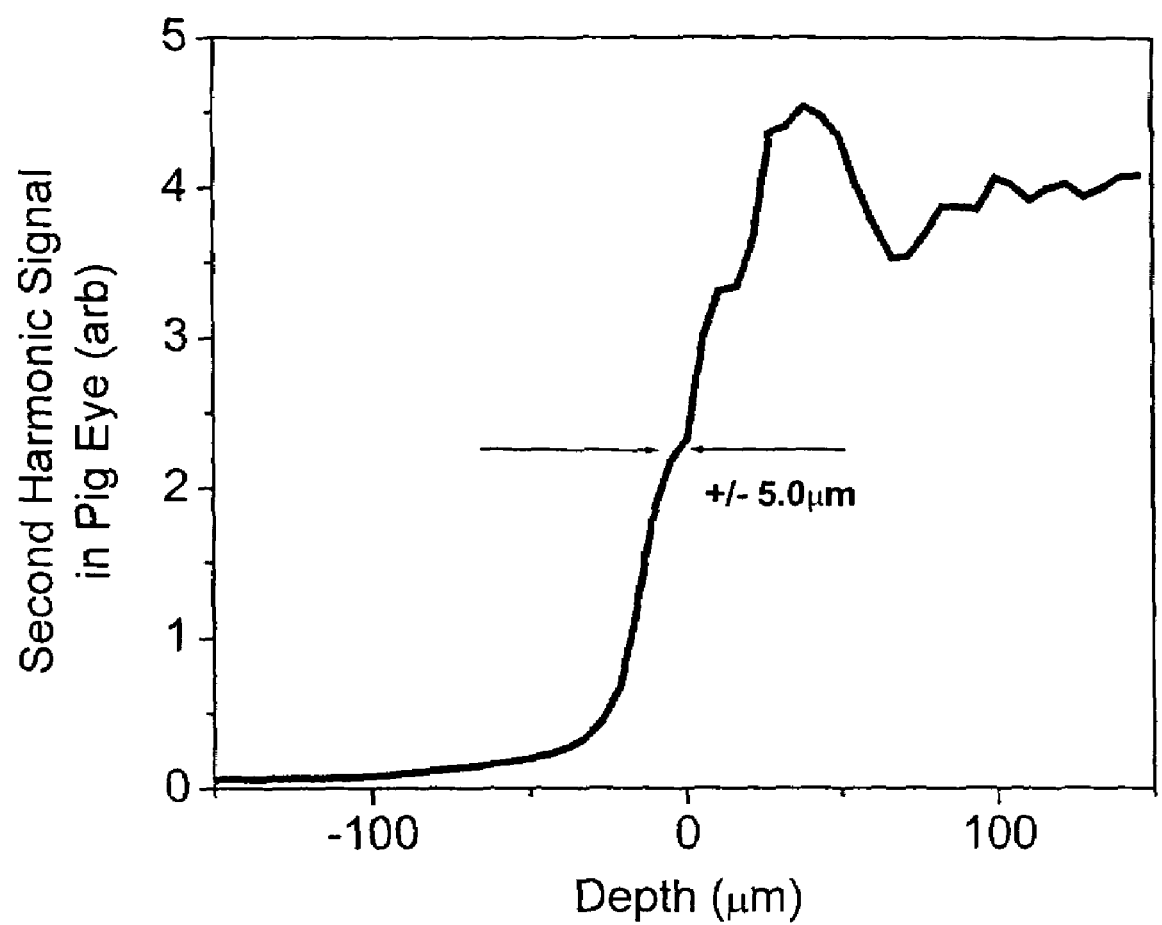
FIG. 6 is a graph illustrating dependence of second harmonic signal on beam waist position in pig eye where the positive sign on the Depth axis corresponds to the position inside the cornea and the zero position corresponds to the cornea-glass interface.

Referring to FIG. 6, the method may be further described. FIG. 6 is a graph illustrating dependence of second harmonic signal on beam waist position in pig eye where the positive sign on the Depth axis corresponds to the position inside the cornea and the zero position corresponds to the cornea-glass interface. To determine the focal point of the laser beam at the interface of the aplanation lens and the cornea, one takes half the max of the signal. This is shown on the graph on at the point of 0 microns. If the focal spot moves out into the aplanation lens, then the signal decreases, if the focal point goes into the cornea, then the signal increases. This can be done because, with certain laser beams, such as a femtosecond mode-locked laser beam can be described by its confocal parameter. In other words, the laser beam has a focal point with a particular length range. It is when half the length of the focal point range is inside the cornea that the signal would be at the half max of the signal.

In one experiment, the method was tested with an aplanation lens in contact with a pig eye. The energy level of laser was reduced to 0.2 □J so that the fluence is below the optical damage threshold of the glass or pig eye, but high enough to generate second harmonic in cornea. While scanning the depth of the focal point, the intensity of second harmonic decreases by factor of 50 from cornea to glass interface. This enabled localization of the focal point at the cornea-glass interface with accuracy of better than +/−5.0 microns. Results are presented on FIG. 6

In another experiment, the method was tested with an aplanation lens having a piece of plastic attached to the lens. The piece of plastic was used to simulate a cornea being in contact with the aplanation lens. The energy level of the laser system was reduced to 0.7 μJ so that the fluence is below the optical damage of the glass, but high enough to generate white light. While scanning the depth of the focal point, the intensity of while light changes by factor of two from glass to plastic. This enable the localization of the focal spot position at the glass-plastic interference with an accuracy of 5 micron.

The inventive systems and methods described above are well adapted for a system to determine the position and alignment of an aplanation lens in relation to a laser system. However, it shall be noted that the foregoing description is presented for purposes of illustration and description, and is not intended to limit the invention to the form disclosed herein. Consequently, variations and modifications to the systems and processes commensurate with the above teachings and teaching of the relevant art are within the scope of the invention. These variations will readily suggest themselves to those skilled in the relevant art and are encompassed within the spirit of the invention and the scope of the following claims.

Moreover, the embodiments described are further intended to explain the best modes for practicing the invention, and to enable others skilled in the art to utilize the invention in such, or other, embodiments and with various modifications required by the particular applications or uses of the present invention. It is intended that the appending claims be construed to included alternative embodiments to the extent that it is permitted by the prior art.

What is claimed is:

1. A method for determining the focus of a laser beam about a surface of an object, the method comprising the steps of:
   providing an object having a substantially planar surface;
   providing a laser system for generating a laser beam;
   focusing a laser beam at or near the substantially planar surface, wherein the laser beam is reflected back from the substantially planar surface;
   detecting a fringe pattern created by interference between the reflected laser beam and a reference beam; and
   extracting a focal position of the laser beam relative to the substantially planar surface using the fringe pattern.

2. The method of claim 1, wherein the detecting step includes:
   providing an interferometer; and
   utilizing the interferometer to analyze the fringe pattern.

3. The method of claim 1, wherein extracting the focal position further comprises:
   determining a fringe curvature sign and a fringe curvature magnitude for fringes within the fringe pattern; and
   determining the focal position from the fringe curvature sign and the fringe curvature magnitude.

4. The method of claim 3, wherein extracting the focal position comprises:
   detecting edges of the fringes within the fringe pattern;
   fitting polynomial curves to the detected edges, wherein each fitted polynomial curve determines an edge curvature sign and an edge curvature magnitude for each respective fringe; and
   averaging the edge curvature magnitudes to determine the fringe curvature magnitude.

5. A laser system for determining the focus of a laser beam about a substantially planar surface of an object, the system comprising:
   a laser system for generating a laser beam, the laser system having a central processing unit, the central processing unit configured for instructing movement of the laser beam;
   an interferometer for detecting a fringe pattern, the interferometer interconnected with the laser system; and
   a software program for execution on the central processing unit, the software program configured for:
      focusing a laser beam at or near the substantially planar surface, wherein the laser beam is reflected back from the substantially planar surface;
      detecting a fringe pattern created by interference between the reflected laser beam and a reference beam; and
      extracting a focal position of the laser beam relative to the substantially planar surface using the fringe pattern.

6. The laser system of claim 5, wherein extracting the focal position further comprises:
   determining a fringe curvature sign and a fringe curvature magnitude for fringes within the fringe pattern; and
   determining the focal position from the fringe curvature sign and the fringe curvature magnitude.

7. The laser system of claim 6, wherein extracting the focal position further comprises:
   detecting edges of the fringes within the fringe pattern;
   fitting polynomial curves to the detected edges, wherein each fitted polynomial curve determines an edge curvature sign and an edge curvature magnitude for each respective fringe; and
   averaging the edge curvature magnitudes to determine the fringe curvature magnitude.

* * * * *